United States Patent [19]

Gray

[11] Patent Number: 5,011,409

[45] Date of Patent: Apr. 30, 1991

[54] POLYURETHANE INTRAORAL DAM

[75] Inventor: Norman Gray, Cary, N.C.

[73] Assignee: Aukland (USA), Inc., Cary, N.C.

[21] Appl. No.: 463,541

[22] Filed: Jan. 11, 1990

[51] Int. Cl.$^5$ ................................................ A61C 5/14
[52] U.S. Cl. ...................................... 433/136; 433/137
[58] Field of Search ................................ 433/136, 137

[56] References Cited

U.S. PATENT DOCUMENTS

| | | | |
|---|---|---|---|
| 3,781,994 | 1/1974 | Hesselgren | 433/137 |
| 4,000,117 | 12/1976 | Shah | 528/48 |
| 4,131,604 | 12/1978 | Szycher | 528/79 |
| 4,463,156 | 7/1984 | McGary et al. | 528/65 |
| 4,523,005 | 6/1985 | Szycher | 528/76 |
| 4,614,787 | 9/1986 | Szycher et al. | 528/75 |

Primary Examiner—John J. Wilson
Assistant Examiner—Cindy Cherichetti
Attorney, Agent, or Firm—Waldron & Associates

[57] ABSTRACT

An improvement in an unitary preassembled intraoral dam for all dental procedures which comprises an extrudable thermoplastic polyurethane which is the reaction product of an aliphatic diisocyanate, a high molecular weight polyether diol, and a low molecular weight aliphatic diol. The improved polyurethane intraoral dam is impermeable to particles of 10 micrometers or greater, with a high degree of puncture and tear resistance, hemocompatibility, hydrolytic stability, non-cytotoxicity, thus guaranteeing the maintenance of a sterile operative field, and a high degree of prevention of contamination and infection for either patient or practitioner.

5 Claims, 1 Drawing Sheet

POLYURETHANE INTRAORAL DAM

BACKGROUND OF THE INVENTION

1. Field of the Invention

The present invention relates to an improvement in a preassembled, molded, disposable intraoral dam for use during dental procedures, the improvement comprising a solution-grade thermoplastic polyurethane composition, which, while retaining the physical properties of natural rubber, latex and other elastomeric intraoral dams, has the added benefit of being impermeable to particles as small as 10 micrometers, hemocompatible, non-cytotoxic, with enhanced puncture and tear resistance, and high tensile strength; in addition, it remains flexible at body temperature without losing its elasticity or strength.

2. The Prior Art

The claimed improvement is a solution-grade thermoplastic polyurethane intraoral dam which comprises a unitary preassembled elastic membrane held taut about the periphery by a complementary annular spring-like frame member, as disclosed in U.S. Pat. No. 4,828,491, May 9, 1989. One of the most undesirable qualities of prior art elastomeric intraoral dams results from pinholes which may occur as a result of the molecular composition of natural vulcanized rubber, and the latex rubber manufacturing process. These pinholes are shown by electron microscopy and X-ray analysis to be large enough (i.e., up to 15 micrometers wide, and up to 30 micrometers deep, in some cases) to allow the transmission of disease-producing pathogens. These studies further show that irregular particles are noted to be deeply embedded in the surface of the elastomer, producing a pitted structure. Other undesirable qualities of elastomers used in prior art intraoral dams include hyperallergic reactions, loss of elastic properties at body temperature, and inadequate puncture and tear resistance. Consequently, while elastomeric intraoral dams of the prior art do tend to provide a limited sterile operative field, it is clear that an intraoral dam produced from an elastomeric product which eliminates the undesirable qualities, as outlined above, is needed in the art. The claimed improvement insures a significantly greater guarantee of a sterile operative field for oral procedures by effectively eliminating the drawbacks encountered in prior art intraoral dams using natural rubber and latex materials.

Of the prior art relating to extrudable thermoplastic polyurethanes for clinical uses, that which is most germane to the claimed improvement is U.S. Pat. No. 4,523,005, June 11, 1985, which teaches an extrudable polyurethane which is the reaction product of an aliphatic organic diisocyanate, a high molecular weight polyether polyol, and 1,4 butane diol. However, this reference only contemplates an extruded polyurethane, and neither suggests nor anticipates solution dipping procedures, as is employed in the claimed improvement. This prior art polyurethane is disclosed in the context of catheters, blood bags, and surgical tubings, and does not suggest any properties of the polymer in films having a thickness suitable for the formation of the intraoral dam of the claimed improvement. Other related patents by the same inventor (Szycher) include U.S. Pat. No. 4,614,787, which discloses a drug dispensing system which uses a polyurethane matrix which is the reaction product of an isocyanate terminated prepolymer and a monomer containing hydroxyl and vinyl groups; U.S. Pat. No. 4,483,759 discloses a flexible elastomeric polyurethane acrylic copolymer which is radiation cured; and U.S. Pat. No. 4,638,043, which discloses a drug releasing system comprising a polyurethane acrylic copolymer which is the reaction product of an oligomer of a diisocyanate, a glycol with molecular weight between the range of 500–5000, and an acrylyl chain terminator, with molecular weight between the range of 40–200, molecular weight units being cured by actinic radiation. These related patents are included as part of the disclosure for informational purposes only, and are not germane to the claimed improvement, as the impact is merely cumulative.

U.S. Pat. No. 4,000,117, Dec. 28, 1976, also discloses a solution-grade thermoplastic polyurethane elastomer. However, this disclosure teaches a polyester-based urethane polymer, while the claimed improvement is a polyether-based urethane, with materially different properties, including greater tensile strength and ultimate elongation before breakage, higher flex fatigue and hydrolytic stability. In addition, the polyether urethane of the claimed improvement shows no degradation in properties over substantial aging periods, either natural or accelerated, while the polyester urethanes disclosed in U.S. Pat. No. 4,000,117 show substantial and immediate degradation of properties on aging.

U.S. Pat. No. 4,463,156, July 31, 1989, discloses a cross-linked, thermoset polyurethane, and is therefore outside the scope of the claimed improvement, which is directed to a thermoplastic polyurethane.

SUMMARY OF THE INVENTION

The present improvement contemplates a unitary intraoral dam constructed of a polyether-based thermoplastic polyurethane which exhibits a very high degree of puncture and tear resistance, hydrolytic stability, low flex fatigue, and an overall tensile strength of about 6900psi, and is impermeable to molecules as small as 10 micrometers, as well as being hemocompatible and non-cytotoxic. The polyurethane is the reaction product of an eliphatic diisocyanate, a high molecular weight polyether diol, and a low molecular weight aliphatic diol.

It is a principal object of the claimed improvement to provide an effective, preassembled molded intraoral dam for use in all dental procedures, comprising a solution-grade thermoplastic polymeric membrane which is impermeable to particles of about 10 micrometers, or greater, in diameter, with high puncture and tear resistance, to maximize patient and practitioner protection against contamination and/or infection from body fluids and the transmission of other disease-producing pathogens.

Another object of the claimed improvement is to provide an intraoral dam with a VICAT softening point at body temperature to minimize rigidity, thereby maximizing patient comfort and ease of manipulation, while retaining its physical properties.

Another object of the claimed improvement is to provide an intraoral dam which is hydrolytically stable, and having very low flex fatigue, further facilitating a continuous sterile operative field.

These and other objects and advantages of the claimed improvement are attained in an intraoral dam fabricated from a noncross-linked, thermoplastic polyurethane elastomeric composition which is the reaction product of an aliphatic diisocyanate, a high molecular weight polyether diol having a molecular weight in the order of about 1,000 to about 5,000 and a low molecular weight aliphatic diol containing about 2 to about 6 carbon atoms, the ratio of polyether diol to aliphatic diol being in the range of about 0.3 to about 1.7, preferably in the range of about 0.7 to about 1.3.

DETAILED DESCRIPTION OF THE PREFERRED EMBODIMENTS

Figure 1:
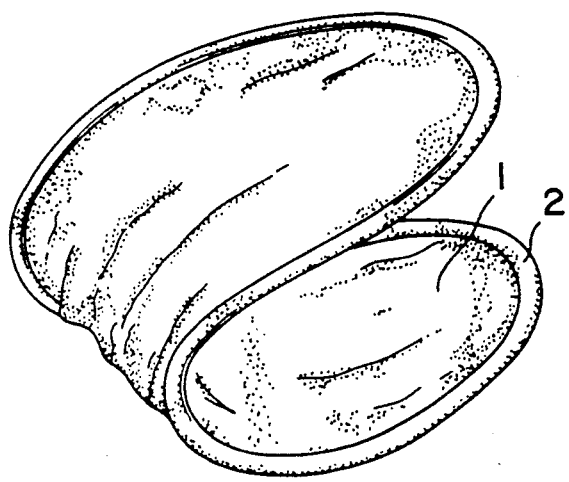
FIG. 1 is a perspective view of an embodiment of the preassembled intraoral dam of the claimed improvement.

The polyurethane composition used for the claimed improvement is a non-cross-linked thermoplastic polymer. The polyurethane solution is made by dissolving solid particles of the polyurethane composition described below in a suitable organic solvent such as tetrahydrofuran, dimethyl acetamide, methylene chloride, or a mixture thereof, at a solids concentration of about 5 to about 25% by weight of the solution, and preferably about 10 to about 20% by weight of the solution. The viscosity at 55 degrees centigrade is 150 to 6500cps, and preferably 2300cps.

After deposition of a film of the polyurethane composition of the desired thickness, it is necessary to allow the solvent to evaporate, whereby a solid continuous polyurethane film is formed.

The solution-grade polyurethane composition of the claimed improvement is prepared by using stoichiometric proportions of the aliphatic diisocyanate reacted with a mixture of the higher molecular weight polyether diol and low molecular weight aliphatic diol in the presence of a small but effective amount of a condensation catalyst such as dibutyl tin dilaurate, the ratio of polyether diol to aliphatic diol being in the range of about 0.3 to about 1.7, preferably in the range of about 0.7 to about 1.3. At such polyether diol/aliphatic diol ratios, the Shore Hardness of the polyurethane elastomer will range from 70 to 90, with a Shore Hardness of 80 preferred for the present improvement.

Aliphatic diisocyanates useful in the practice of the present invention have the formula:

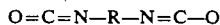

where R is a cycloaliphatic radical having 1 to 6 carbon atoms in a methylene bridge connecting 4-cyclohexyl isocyanates moieties and represented by the formula:

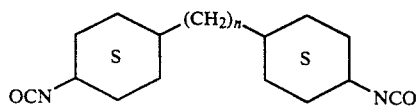

where N=1-6. An illustrative example of such aliphatic diisocyanates is methylene bis (4-cyclohexyl) isocyanate, (HMDI), which is preferred.

Aliphatic polyether diols useful in the practice of the present improvement range in average molecular weight from about 1,000 to about 5,000, the aliphatic group in the polyether diol preferably containing about 4 to about 12 carbon atoms, the aliphatic group being straight chain, or branched or cyclic. Illustrative polyether diols useful in the practice of the present improvement include polytetramethyl ether glycol having a molecular weight in the range of 1,000 to 2,000.

An intraoral dam prepared in accordance with the preferred form of the claimed improvement will ideally have the following properties within the ranges as specified:

| | |
|---|---|
| Permeability | Non-permeable to 10M-sized particles |
| Hardness | 80A (Shore) |
| Ultimate elongation | 720 percent |
| Ultimate tensile strength | 6900 psi |
| VICAT softening point | 54° C. |
| Hydrolytic stability | Hydrolytically stable |
| Stress at 500 percent | 2250 psi |
| Molecular base | Polyether |

Both natural and accelerated aging tests showed that the polyurethane composition comprising the claimed improvement constantly maintained the above properties over an extended period of time.

Figure 2:
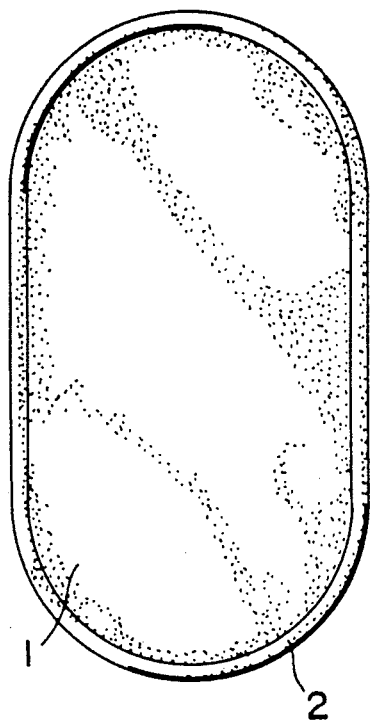
FIG. 2 is a plan view of the intraoral dam shown in FIG. 1.
Figure 3:
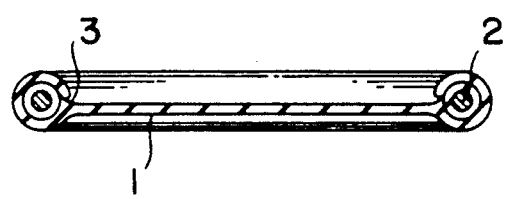
FIG. 3 is a cross-sectional view of the intraoral dam taken along the line III—III of FIG. 2.

Referring to the drawings, the preassembled intraoral dam of the claimed improvement is a unitary structure comprising two basic components, namely, a shaped elastic membrane 1 and a complementary annular spring-like frame member 2 (see FIGS. 1 and 2). The peripheral portion of the elastic membrane 1 is wrapped around the spring-like frame member 2 and secured in place by adhesive 3 (see FIG. 3) in a manner described below.

The intraoral dam may be assembled in any convenient manner without departing from the claimed improvement. The following is a description of a best mode for producing the dam from the thermoplastic polyurethane composition described above.

The membrane and spring-like frame member may be made on a computer-generated shaped mold having a substantially flat surface of predetermined peripheral shape and side surfaces extending transversely from the periphery of the flat surface. The computer-generated shape is calculated on the basis of measurements from various human oral cavities displayed in one mathematical plane. The mold is momentarily dipped into a solution of thermoplastic polyurethane composition of the claimed improvement, as outlined above, to form a film on the mold flat and side surfaces. The mold with the film is then placed in an oven to dry and cure the mixture to form the membrane. The membrane is then stripped from the mold and dried.

The intraoral dam may be washed prior to non-sterile packaging, or can be sterilized and then individually sterile-packed for distribution to dentists and dental technicians.

In use, if the dental practitioner desires to isolate one tooth or a series of teeth, a suitably sharp device or punch may be used to cut one or more small holes in the membrane 1 medial to the frame member 2 of the intraoral dam, the location of the one or more holes corresponding to the teeth to be isolated. A smear of lubricant over the one or more holes is recommended for easier installation. The intraoral dam is then folded in half, squeezed into fourths and inserted into the oral cavity of the patient. The device acts in the manner of a spring and reopens itself to the half-folded position shown in FIG. 1, due to the resilient nature of the spring-like frame member 2. This spring or restoring action continues to cause the dam to tend to open itself to its original flat position shown in FIG. 2, and helps maintain the patient's mouth in an open position. The frame member fits radially to the teeth. If for some reason the dentist or dental technician has difficulty inserting the device, the patient can be easily taught to insert the device.

Once the device is positioned in the oral cavity, the dentist or dental technician can complete the installation of the device by stretching the punched membrane around the isolated teeth. The frame spring action pushes the membrane with a maximum force around the isolated teeth such that the membrane is held taut beneath the border of the crown-gum line of the isolated teeth. Dental floss may be used by the dentist or dental technician to force the membrane material round occluded teeth. No clamps are necessary to hold the dam or the membrane itself around the isolated teeth.

If the dentist or dental technician desires to install the device in a totally intraoral fashion, one or more holes may be punched at the respective locations in the elastic membrane to facilitate such installation. If the dentist or dental technician desires to install the device such that a tooth or a series of teeth may be isolated, and additionally, if the upper or lower lips are to be covered and retracted, one or more holes may be punched in the corresponding positions in the elastic membrane, such that when the intraoral dam is installed the device protrudes from the oral cavity and covers and retracts the upper lips, lower lips, or both. The multi-directional flexibility of the dam allows it to adjust to any size mouth opening with no comfort loss to the patient.

Figure 4:
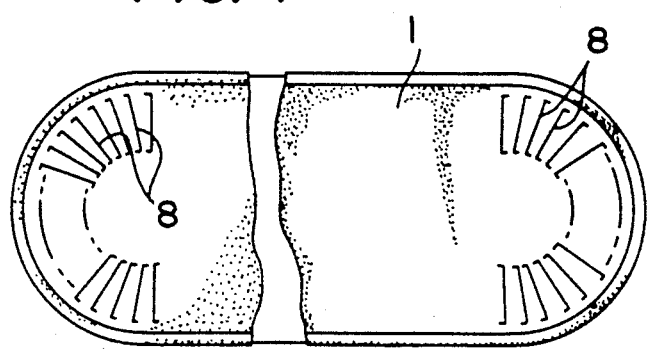
FIG. 4 is a plan view of another embodiment of the intraoral dam of the claimed improvement.
Figure 5:
FIG. 5 is a cross-sectional view of a rib of the intraoral dam shown in FIG. 4.

A further embodiment of the claimed improvement is shown in FIGS. 4 and 5 wherein the membrane 1 is formed with a series of ribs 8. The ribs are arranged such that a pair of ribs coincide with the location of a tooth. These ribs are arranged along a radial axis perpendicular to and adjacent the spring-like frame member is an annular configuration. Thus, eighteen ribs, a pair for each tooth per upper or lower jaw, are formed in the membrane. A cross-sectional view of a rib 8 is illustrated in FIG. 5. The ribs are triangular in shape, the size of one side of the triangle being about 0.0018 inch. The ribs facilitate installation between occluded teeth and facilitate insertion around widely spaced teeth.

It will be evident to those skilled in the art that alternate embodiments and modifications may be made herein which fall within the scope of the claimed improvement.

I claim:

1. In a unitary preassembled disposable intraoral dam having a flexible elastic membrane held taut about its periphery by a complimentary annular spring-like frame member, the improvement comprising an extrudable thermoplastic polyurethane composition, said composition being the reaction product of an aliphatic diisocyanate, a high molecular weight aliphatic polyether diol, said aliphatic polyether diol having a molecular weight in the range of about 600 to about 5,000, and a low molecular weight aliphatic diol containing about 2 to about 6 carbon atoms, wherein the molar ratio of said polyether diol to said aliphatic diol is in the range of about 0.3 to about 0.7.

2. The improvement of claim 1, wherein said aliphatic diisocyanate is methylene bis (4-cyclohexyl) isocyanate.

3. The improvement of claim 1, wherein said aliphatic diol is 1,4-butane diol.

4. The improvement of claim 1, wherein the preferred molar ratio of polyether diol to aliphatic diol is about 0.7 to about 1.3.

5. The improvement of claim 1, wherein said polyurethane has a VICAT softening point at body temperature.

* * * * *